United States Patent [19]

Teass, Jr.

[11] Patent Number: 4,549,141
[45] Date of Patent: Oct. 22, 1985

[54] SALINITY INDICATOR SYSTEM

[76] Inventor: Horace A. Teass, Jr., 25 Mead Rd., Armonk, N.Y. 10504

[21] Appl. No.: 427,696

[22] Filed: Sep. 29, 1982

[51] Int. Cl.[4] .......................................... G01R 27/22
[52] U.S. Cl. .................................. 324/441; 340/502; 340/603
[58] Field of Search ..................... 340/500, 502, 603; 324/439, 441, 450

[56] References Cited

U.S. PATENT DOCUMENTS

| | | | |
|---|---|---|---|
| 2,565,501 | 8/1951 | Ingram | 324/439 |
| 3,029,379 | 4/1962 | Ingram | 324/441 |
| 3,131,346 | 4/1964 | Parke | 324/441 |
| 3,188,561 | 6/1965 | Ingram | 324/439 |
| 3,263,224 | 7/1966 | Berman et al. | 340/603 |
| 3,965,414 | 6/1976 | Teass, Jr. | 324/441 |
| 4,190,827 | 2/1980 | Diamond | 340/500 |
| 4,383,221 | 5/1983 | Morey et al. | 324/439 |

Primary Examiner—James L. Rowland
Assistant Examiner—Daniel Myer
Attorney, Agent, or Firm—Peck & Peck

[57] ABSTRACT

A salinity indicatory system useful to monitor variations in the salt content of water sources provides for the simultaneous monitoring of a plurality of test stations and the operation of automatic alarm and dumping means when salinity concentrations reach or exceed predetermined set points. The alarm and dump set points are capable of being set at different levels to provide for an indication of an approaching dump condition. The system includes temperature compensating networks having thermistors and associated resistor networks mounted inside the salinity cell to function both as temperature shaping resistors and electronic scaling resistors, thereby providing the system with multi-range capability. A summary fault alarm circuit allows all alarm conditions occurring with respect to any of a plurality of perimeters to be signaled through a single, summary fault relay. An automatic alarm update feature permits alarm conditions subsequent to the first alarm to be signaled at the system console and indicated as subsequent alarm conditions unacknowledged. The system provides an alarm acknowledge feature whereby an alarm condition actuates a bell and flashing light alarm and, when the operator acknowledges the alarm condition, the bell goes off and the alarm lamp goes from flashing on to steady on.

16 Claims, 10 Drawing Figures

SALINITY INDICATOR SYSTEM

TECHNICAL FIELD

The present invention relates to salinity monitoring systems and, more particularly, to a system for monitoring the salinity content in liquid systems carrying water.

BACKGROUND OF THE INVENTION

In many industrial applications involving the use of water, it is essential that the salinity concentration of impurities within that water system be under constant surveillance to provide instant alarming in the event that predetermined concentration limits are reached or exceeded. An example of a particular application in which salinity monitoring is essential is in fluid lines carrying water for use in ship systems where high salinity impurity of the water is potentially dangerous and destructive. Usually, such salinity monitoring systems are installed at unmanned locations and are monitored at remote locations by means of meters, indicators, warning lights and alarms.

In shipboard monitoring systems, it is essential that impurities of a very low order be immediately detected and signaled so that remedial steps can be initiated to avoid substantially damage to the system equipment. It is desirable, therefore, that the monitoring equipment provide effective, dependable and precise continuous sampling at all test locations at which impure concentrations may develop and to provide arrangements for attracting the attention of operating personnel to initiate remedial steps without delay. Additionally, the system should provide for constant indication of salinity concentration and for operating alarms in the event that predetermined levels of concentration impurities are reached or exceeded. The monitoring equipment should also provide for automatic dumping of the contaminated water without the delay necessarily involved when personnel must intervene. Some methods and systems have been suggested for providing surveillance of this type; however, these prior art systems have proved to be inadequate because of the very low order concentrations of impurities which must be detected in view of the variable factors for which such systems must compensate in order to provide the needed degree of precision.

It is generally recognized that as the concentration of salinity decreases, the resistive response of water to temperature changes increases. Tests data indicate an increase of water sensitivity in the order of thirty percent as between pure water and ultra-pure water. Thus, one fixed temperature compensation technique will not compensate for the various ranges of salinity encountered. Since a one-thermistor and one-resistive network will not produce optimum performance except for one purity of water, the temperature compensation technique must be adapted for each purity of water encountered in order to produce high precision compensation. The typical prior art method of handling this temperature compensation problem has been to shape the compensating thermistor with a resistive network located in the electronic panel and to switch between the various compensating networks as different water purity ranges are encountered. In the present invention the special shaping resister network and thermistor are mounted inside the cell and function both as to shape the response for the water and for scaling the electronics.

Some prior art salinity monitors function for the dual purpose of providing a trigger alarm to indicate an impure water condition and also to cause dumping of the impure water. These prior art salinity monitors have provided control panels having these two set points the same or related in some manner. It would be helpful to have a salinity monitoring system having independent set level controls for the alarm function and for the dump function. By having early warning of a pending out of limits water condition, it would be possible to adjust plant operation to correct the problem without having to actually dump and waste water. Also, it would allow operating personnel to schedule corrective action at a convenient time. Therefore, it would be an improvement over the prior art to have a salinity monitoring system having a dump trigger level set at a specified water limit and an alarm level set at a somewhat more sensitive level so as to cause the system to alarm to indicate a pending out of limits condition prior to the time the dump action is triggered.

Typical prior art salinity monitoring systems usually provide one alarm lamp per engine room console and that single alarm lamp signals only abnormal salinity conditions to the exclusion of other alarm conditions such as low temperature, insufficient pressure on various pumps, purging cycle and process and out of limits pH. The prior art salinity monitors have no summary alarm means for signaling alarm conditions involving these other perimeters. It would be helpful to have all alarm conditions signaled through a signal relay, an alarm relay.

Typical prior art salinity monitoring systems have the panel remotely located from the engineer watch station so that the alarm signal must be electrically transmitted to the engineer via the console flashing alarm. A high salinity condition on any of several channels causes the console to go into an alarm situation and the engineer acknowledges the situation by controls at the engineering console. In the typical prior art salinity panel, a subsequent salinity alarm occuring on any of the other channels would not cause the engineering console to realarm if the first alarm situation had not been cleared. While the salinity monitor would indicate this new alarm situation locally, it would not signal such subsequent alarm situation at the watch station. It would be helpful in salinity monitoring systems to provide not only high salinity situations, but also dumping conditions, low pressure and below normal temperatures at the console.

Typical prior art salinity monitoring systems, particularly those involved in marine application, provide for an alarm acknowledge function whereby a watchstander notes an alarm condition, identifies the cause and acknowledges the alarm condition. When the alarm condition is acknowledged, the audible alarm is silenced and the alarm indicator lamp goes from blinking to steady-on in preparation for receiving another alarm condition. In marine salinity monitors which are required to sense not only salinity, but also pH, low temperature, purge cycle, dumping and low pressure, a technique of alarm acknowledgement is needed.

SUMMARY OF THE INVENTION

It is therefore an object of the present invention to provide a salinity indicator system for monitoring salinity content of water sources.

It is a further object of the present invention to provide a salinity indicator system having the thermistor and special shaping resister networks mounted inside the conductivity cell thereby enabling cell substitution, minimizing parts mix-ups and permitting the electronic panel to be designed for multi-range application and adapting the system for easy multi-range application.

It is a further object of the present invention to provide a salinity indicator system having independent set level control points for the alarm function and the dump action function whereby early warning of a pending out of limits water condition is signaled prior to the time a dump action is performed.

It is a further object of the present invention to provide a salinity indicator system having a summary fault alarm circuit whereby alarm conditions involving each of the several perimeters are signaled through a single alarm relay.

It is a further object of the present invention to provide a salinity indicator system having an automatic alarm update capability whereby alarm conditions occurring subsequent to the first such condition are signaled to the watch station console and indicated as subsequent alarm conditions.

It is a further object of the present invention to provide a salinity indicator system having an alarm acknowledgement capability whereby alarm conditions occuring subsequent to a first such alarm condition must be acknowledged before the system will stop indicating the subsequent alarm condition.

It is a further object of the present invention to provide a salinity indicator system wherein stability of operation with reference to relay operations for actuating the alarming and dumping functions is achieved and wherein the relay circuit design permits replacement of relays having different operating characteristics therefrom without disturbing the overall accuracy and stability of the system.

It is a further object of the present invention to provide a salinity indicator system having individual visual and audible alarm functions associated with each of a plurality of monitoring stations wherein alarm conditions at any one location will not effect the monitoring capacity of the remaining locations, thereby permitting the entire system to be constantly monitored while corrective action is taken at a particular monitoring location.

It is a further object of the present invention to provide a salinity indicator system wherein readings upon the metering system are provided against a scale, thereby materially increasing the accuracy of the readings from the system operated over the working portion of the meter dial.

It is a further object of the present invention to provide a salinity indicator system having the capability of providing an input test signal simulating operating conditions of the system and setting alarms under automatic temperature compensation without utilizing extraneous test equipment.

It is a further object of the present invention to provide a salinity indicator system whereby temperature compensating means for compensating temperature effects upon the salinity of the liquid under test is provided by auxiliary resistive network circuits located solely in the conductivity cell.

It is a further object of the present invention to provide a salinity indicator system as a switch arrangement for each conductivity cell location up to ten, whereby a plurality of locations are selectively made available without the necessity for changing the sensing cell units.

It is a further object of the present invention to provide a salinity indicator system having a rotary selector switch arrangement and associated circuitry to permit instantaneous reading of the condition of any of a plurality of monitoring cell locations without disturbing the supervisory alarming of the system, thereby providing for uninterrupted surveillance during meter reading operations regardless of switch position.

It is a further object of the present invention to provide a salinity indicator system which operates at low voltage and current densities thereby avoiding shock hazards and deleterious effects of high voltage and current concentrations at monitoring cell locations and in the associated circuitry.

In accordance with the present invention, the salinity indicator system employs a plurality of salinity conductivity cells immersed at selected locations in a fluid system which must be monitored and controlled. Each such cell comprises a pair of space electrodes which are in contact with the fluid to be monitored and which are connected to a suitable source of ac electric current so that variations in the electrical admittance of the fluid affect the flow of current between the electrodes. The salinity cells also include temperature compensating means in the form of a resistance element having a negative temperature coefficient such a thermistor, in parallel with the meter circuit and in series with the cell electrodes and alarm circuits, in order to accurately compensate for variations in the admittance of the fluid due to temperature effects as distinguised from salinity effects. Complete temperature compensation and correction for the salinity cells is provided by the present invention by placing the thermistor and compensating network inside the salinity cell. Positioning of the compensating circuitry inside the cell allows universal electronic circuitry to be used with a tailored, compensated cell. Thus, saline solutions ranging from the ultra-pure to the brackish range can be handled with high accuracy by means of the same electronic circuits.

A source of electrical power is provided for actuating the monitoring alarm and relay devices and the conductivity cell is interposed in the flow path of current from such power source to these devices to correlate the differences in current response to the differences in degree of salinity of the fluid whereby the monitoring and control devices are actuated.

BRIEF DESCRIPTION OF THE DRAWINGS

The above and still further objects, features and advantages of the present invention will become apparent upon consideration of the following details of the description of a specific embodiment thereof, especially when taken in conjunction with the accompanying drawings wherein.

DESCRIPTION OF THE PREFERRED EMBODIMENTS

Figure 1:
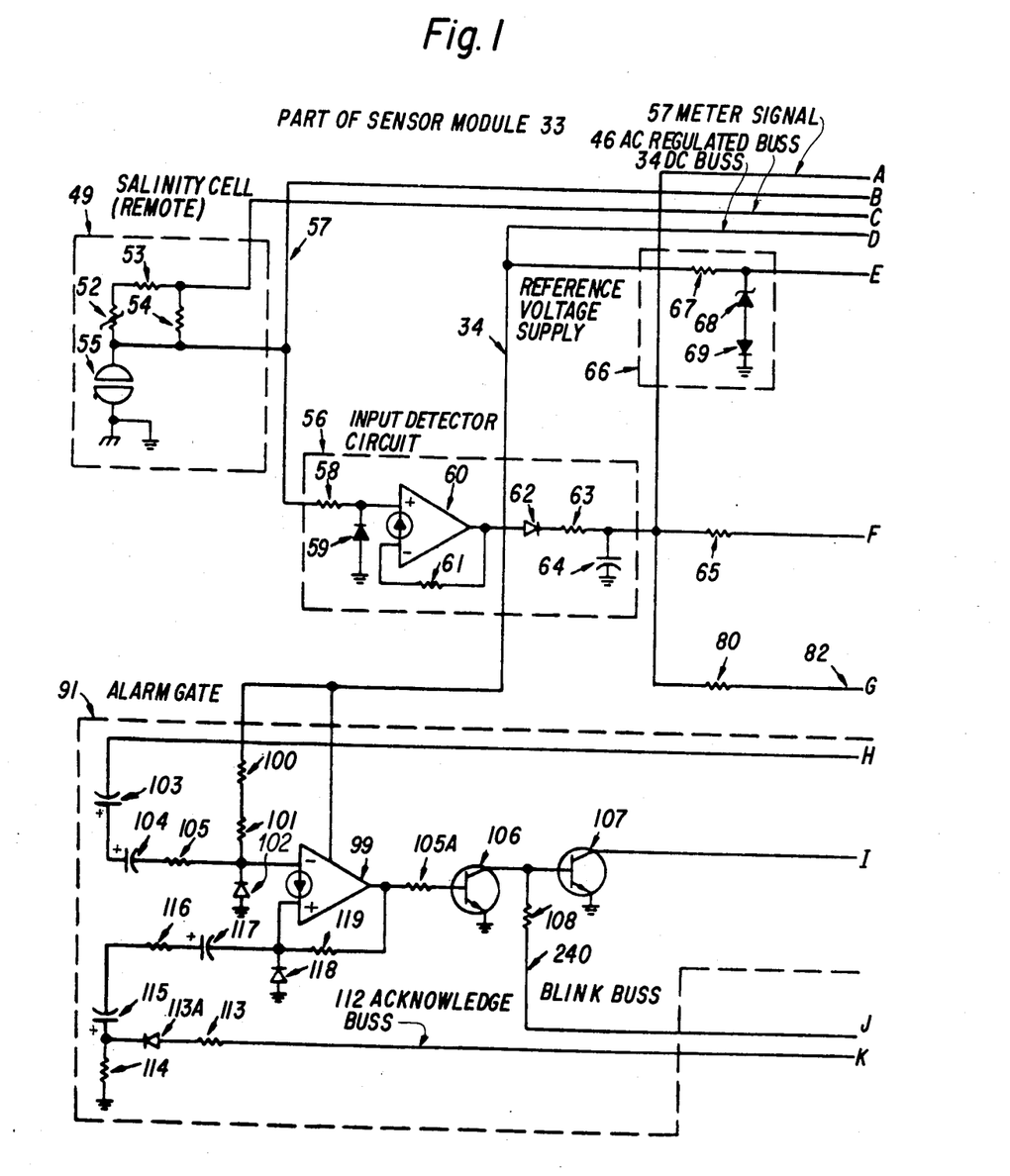
FIG. 1 is a schematic circuit diagram of part of the sensor module of the solid state salinity indicator system of the present invention.
Figure 1A:
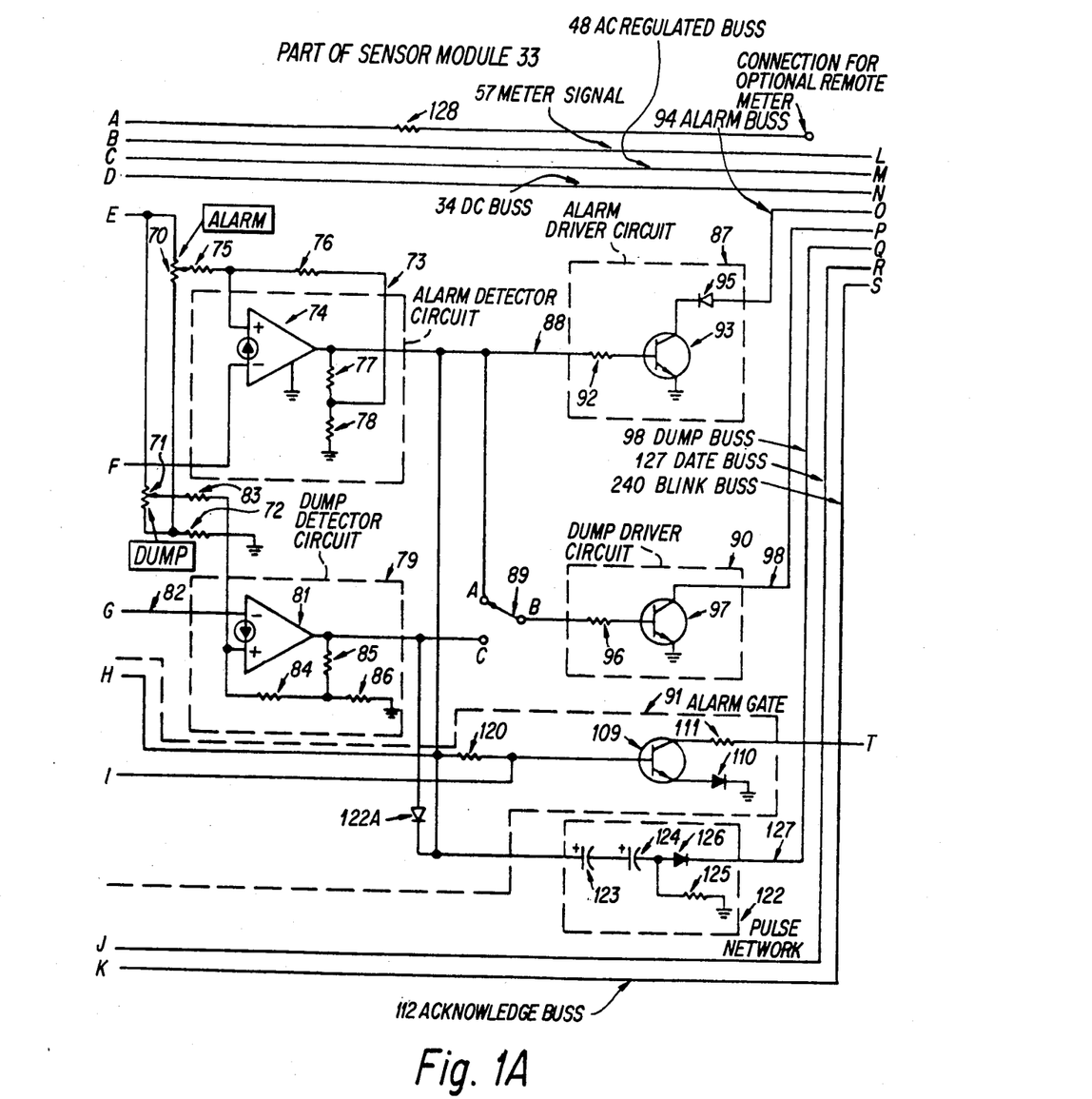
FIG. 1A is a schematic circuit diagram of part of the sensor module of the solid state salinity indicator system of the present invention.
Figure 1B:
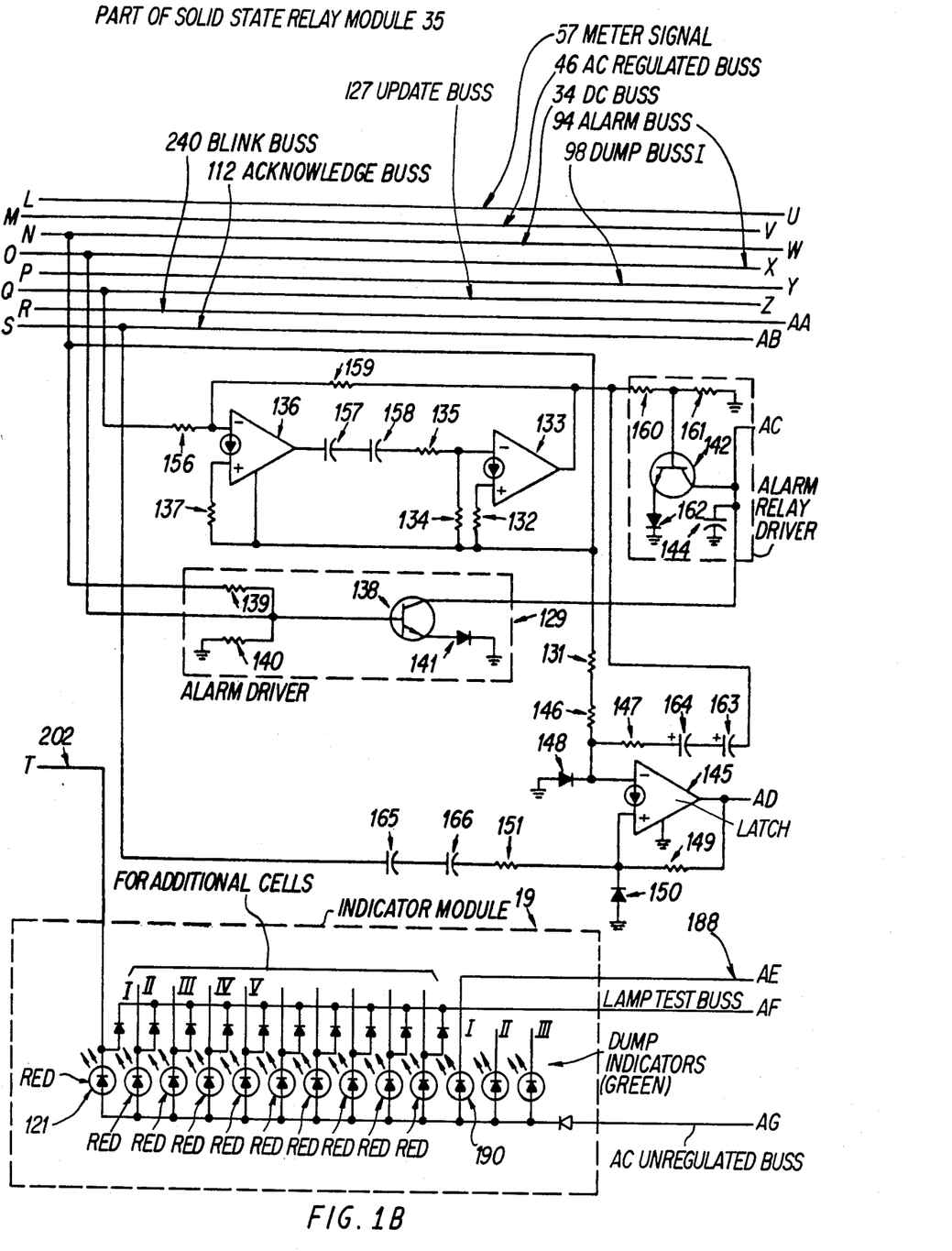
FIG. 1B is a schematic circuit diagram of part of the solid state relay module of the solid state salinity indicator system of the present invention.
Figure 1C:
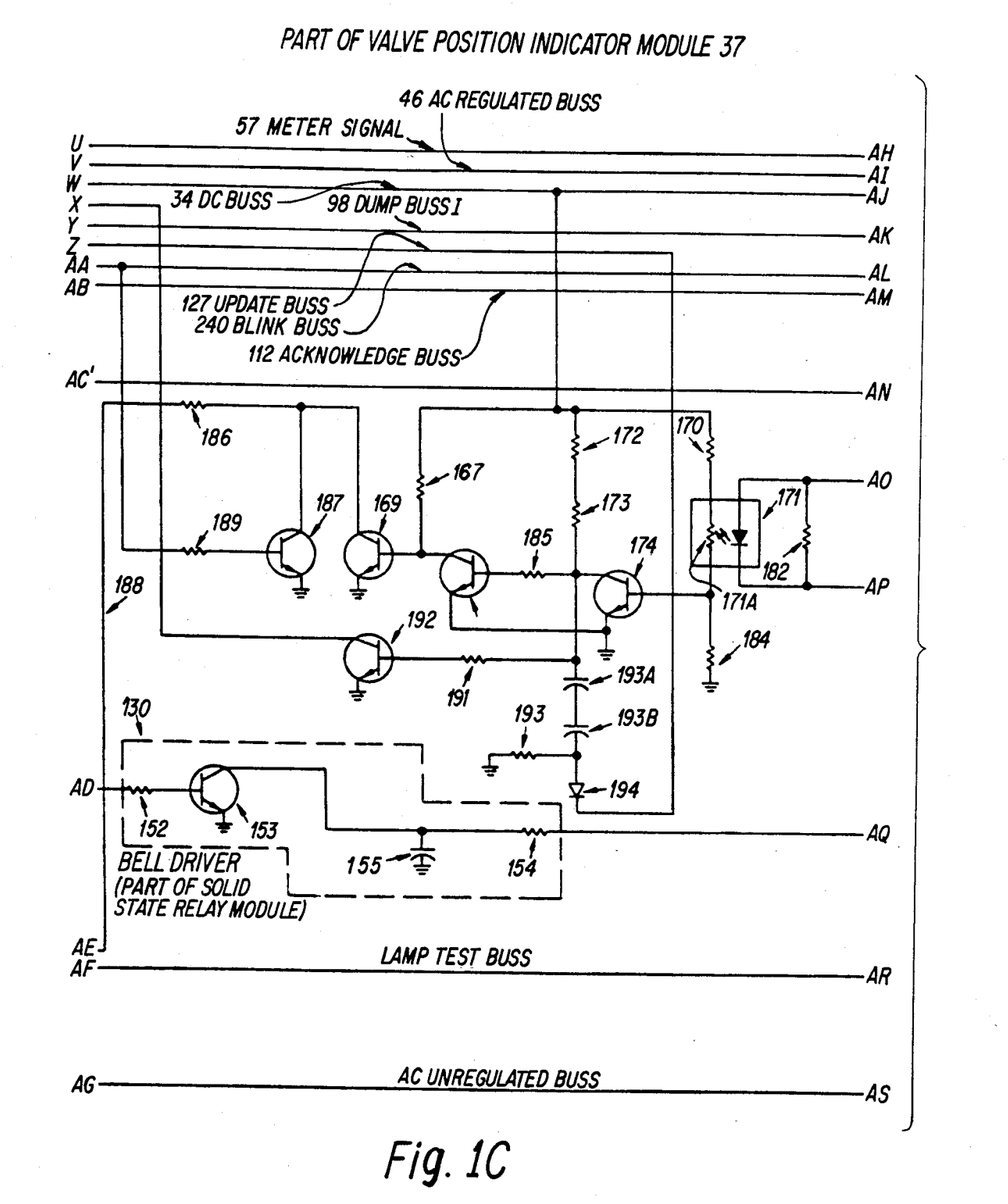
FIG. 1C is a schematic circuit diagram of part of the valve position indicator module of the solid state salinity indicator system of the present invention.
Figure 1D:
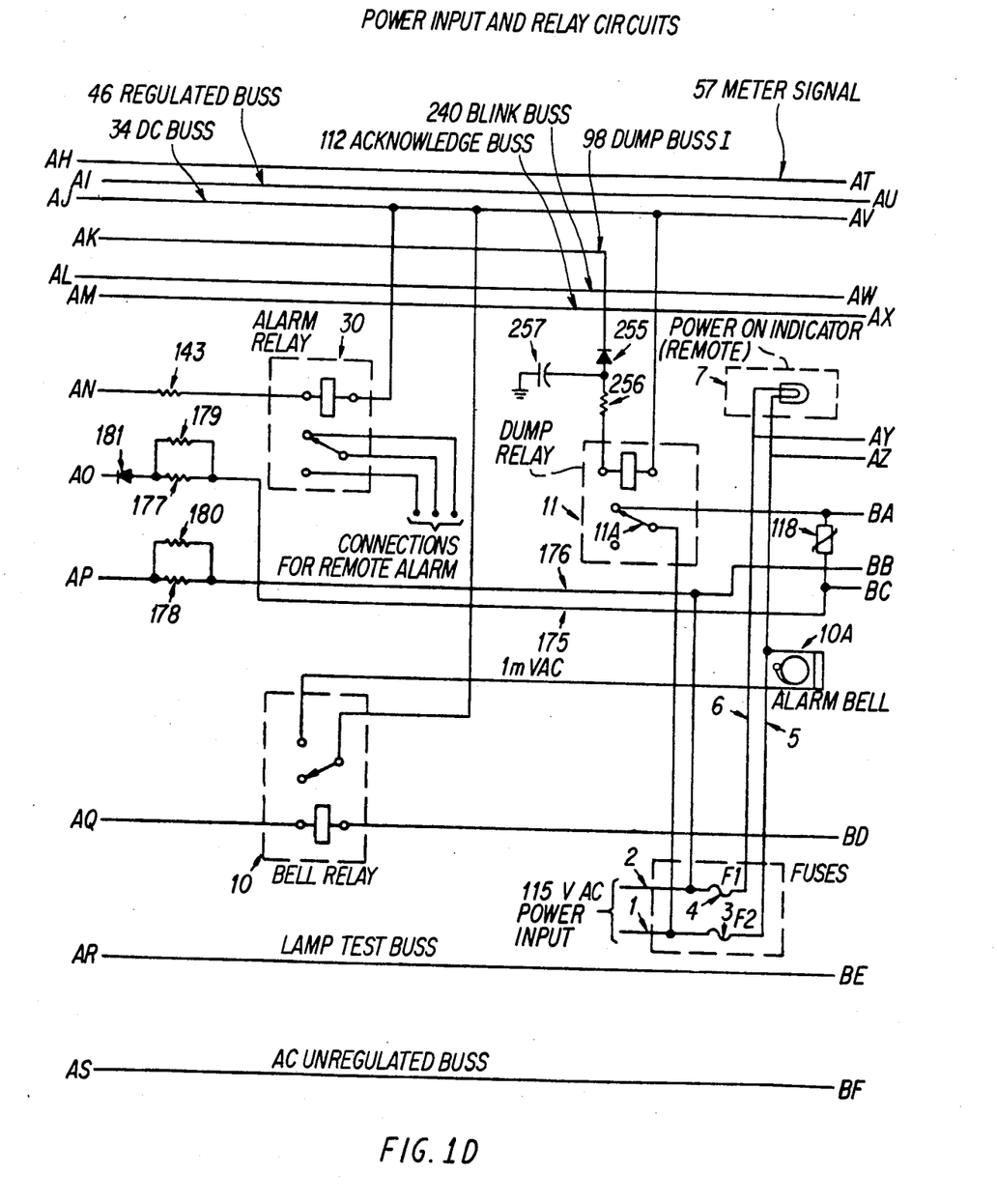
FIG. 1D is a schematic circuit diagram of the power input and relay circuits of the solid state salinity indicator system of the present invention.
Figure 1E:
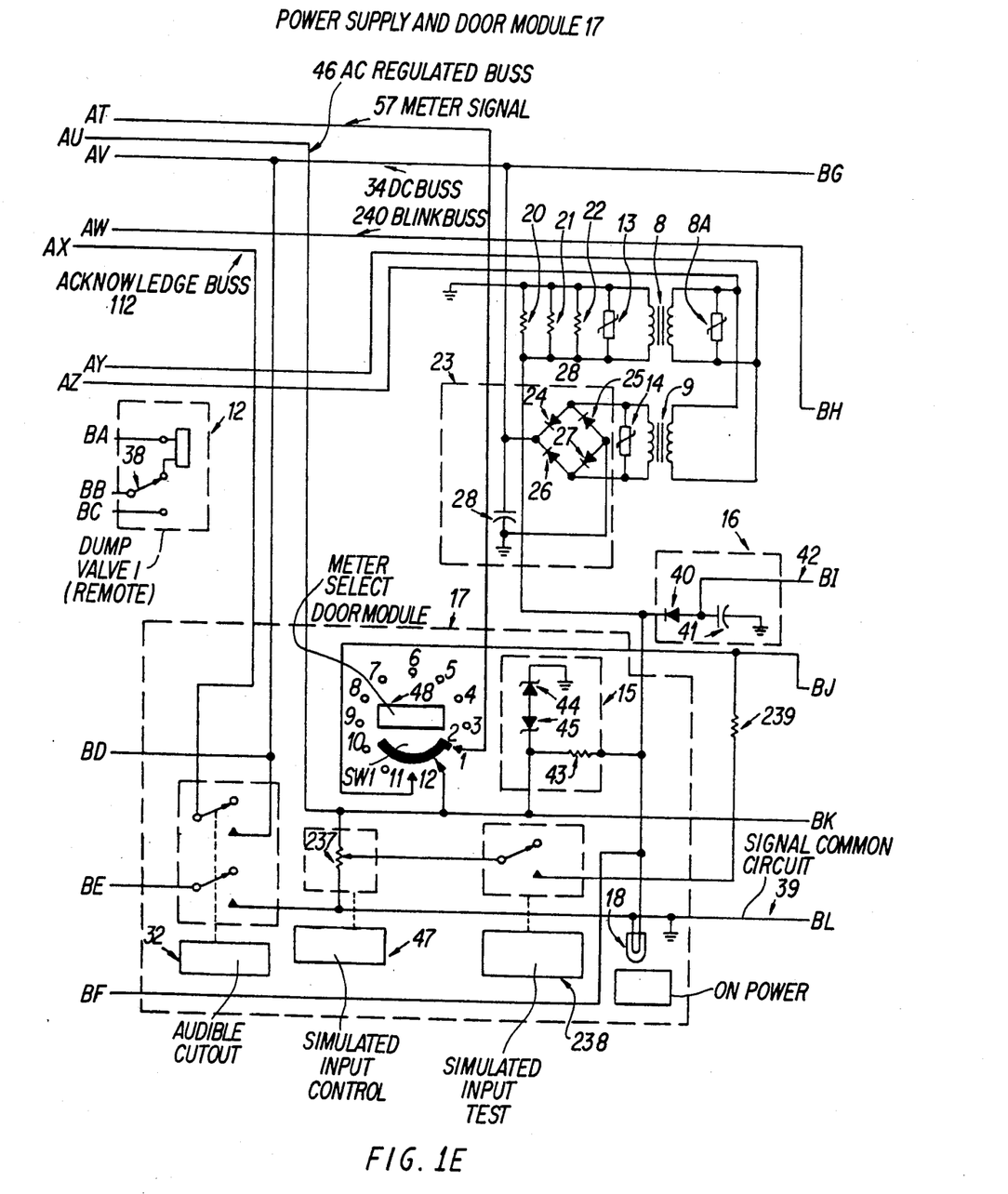
FIG. 1E is a schematic circuit diagram of the power supply and door module of the solid state salinity indicator system of the present invention.

In this description of the preferred embodiments, a signal common circuit lead 39, FIG. 1E, provides the return circuit for each internal low voltage power source and each operating signal circuit. Thus, as a signal or power source is discussed, it will be understood to be with respect to the signal common circuit lead 39.

Referring to the drawings in greater detail, electrical power is fed from a suitable source (not shown) through leads 1 and 2, FIG. 1D, through fuses 3 and 4 which serve to protect the electrical system from malfunctions in the form of exessive current drain. Power is distributed through leads 5 and 6 to a remote power ON indicator 7 and also to step down transformers 8 and 9, FIG. 1E.

The external power input source is also distributed to relay arm 11A of a dump relay 11, FIG. 1D, and is also supplied to a dump valve 12, FIG. 1E. A varistor 11B is connected across dump valve 12 to provide transient voltage protection to prevent accidental damage when dump valve 12 cycles on or off. A varistor 8A is connected across transformers 8 and 9 to provide transient voltage protection for the transformers.

The secondary winding of step down transformer 8 constitutes a low voltage ac power source which supplies low voltage ac power to the following circuits: ac regulator circuit 15, FIG. 1E, negative dc supply 16, door module 17, POWER ON indicator 18, FIG. 1E, and an alarm indicator module 19, FIG. 1B. Resisters 20, 21 and 22, FIG. 1E, are connected in parallel with the secondary winding of step down transformer 8 to provide an option for the user when a 220 volt ac external power source is to be used rather than a 115 volt ac external power source (when the primaries of the step down transformers are series connected).

Varistors 13 and 14, FIG. 1E, are connected across the output windings of step down transformers 8 and 9, respectively, to provide transient voltage protection for circuits powered by these transformers.

The secondary winding of step down transformer 9 provides unregulated low voltage ac power to a dc power supply 23, FIG. 1E, comprising diodes 24, 25, 26, and 27 and capacitor 28. This circuit is a full wave rectifier that converts the ac power from step down transformer 9 to a direct current that is filtered by capacitor 28. This dc power source supplies plus 30 vdc to dc voltage bus 34, FIG. 1E, and it provides the operating power required by the following circuits and components of the salinity system: bell relay 10, FIG. 1D, alarm relay 30, FIG. 1D, solid state relay meter module 31, FIGS. 1F and 1G, audible cutout switch 32, FIG. 1E, sensor module 33, FIGS. 1 and 1A, solid state relay module 35, FIG. 1B, dump relay 11, FIG. 1D, and valve position indicator 37, FIG. 1C.

Figure 1F:
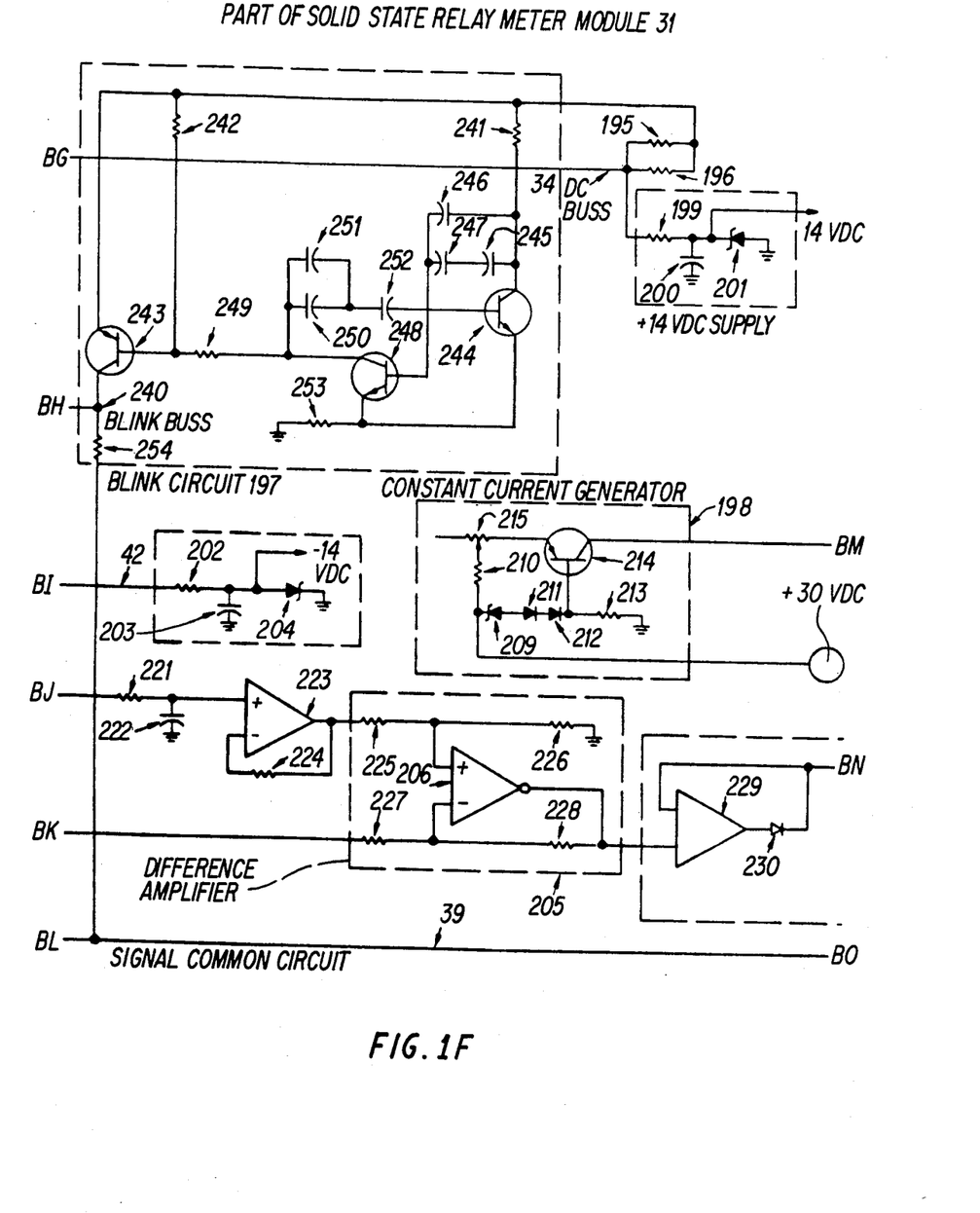
FIG. 1F is a schematic circuit diagram of part of the solid state relay meter module of the solid state salinity indicator system of the present invention.
Figure 1G:
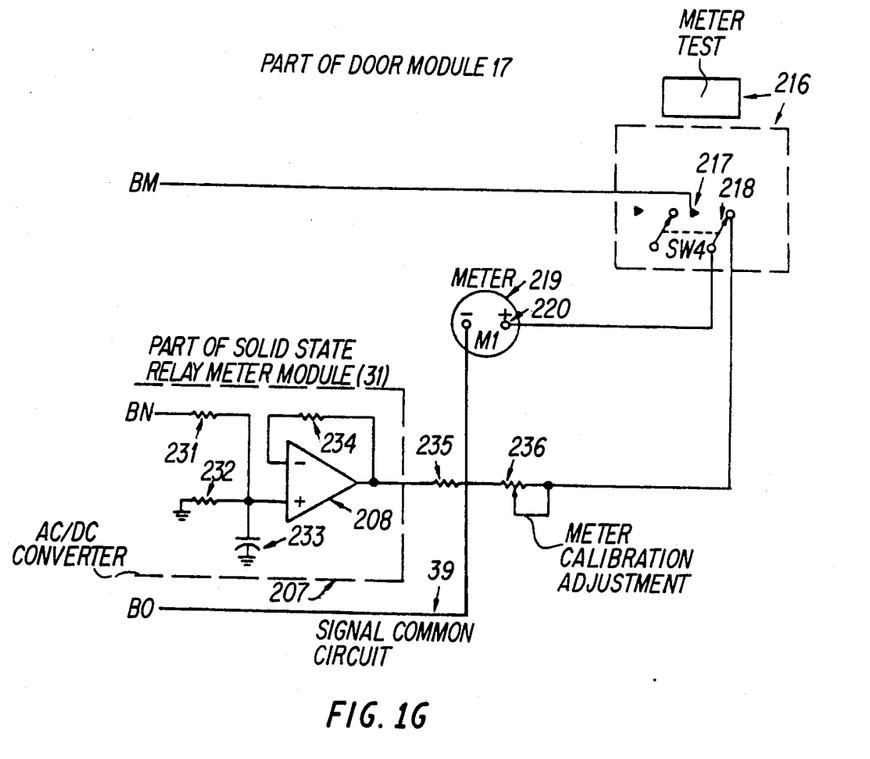
FIG. 1G is a schematic circuit diagram of part of the door module of the solid state salinity indicator system of the present invention.

A negative voltage supply 16, FIG. 1E, is provided to furnish a −14 vdc voltage source for solid state relay meter module 31, FIGS. 1F and 1G. This supply is developed from the output of step down transformer 9, by means of diode 40 and filter capacitor 41, FIG. 1E.

An ac regulator circuit 15, FIG. 1E, provides a low voltage regulated ac supply for sensor module 33, FIGS. 1 and 1A, solid state relay meter module 31, FIGS. 1F and 1G, and door module 17, FIG 1E. The ac regulator circuit 15 consists of resistor 43 connected between stepdown transformer 9 and back-to-back connected zener diodes 44 and 45.

In the circuit illustrated in FIGS. 1 through 1G, a system employing one salinity cell is illustrated. However, it will be understood that the instant invention is not limited to the employment of a single such cell and that the inventive features herein to be described may be employed in connection with a single or any number of salinity cell units.

A salinity cell is provided with an associated sensor module 33, FIGS. 1 and 1A, and monitoring circuit network. A one cell system will be described herein and it will also be understood that the number of cells may be varied in accordance with the requirements of a particular application and that it is a feature of this invention that said variations may be readily and efficiently accomplished.

Figure 2:
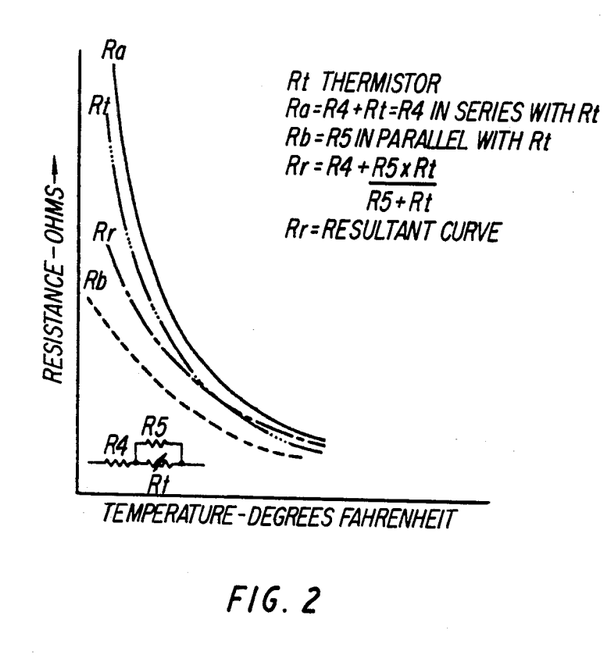
FIG. 2 is a graphic representation of the temperature-resistence response characteristic of the temperature compensation network used in the present invention.
Figure 3:
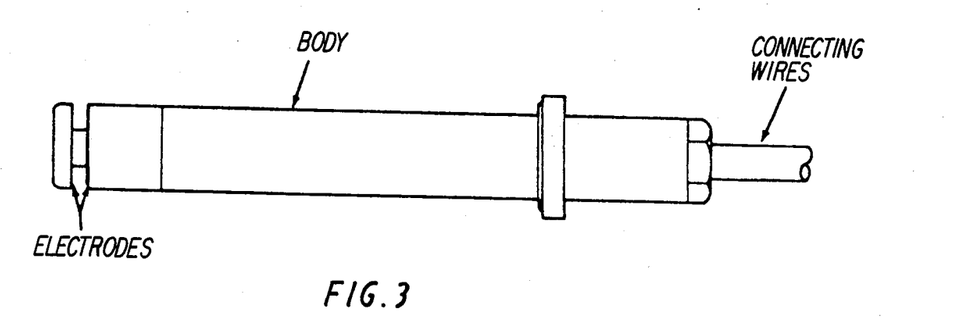
FIG. 3 is a side elevation view of a salinity conductivity cell.

An excitation signal for salinity cell 49, FIG. 1, is routed from ac regulated bus 46. Resistor 53, connected in a series/parallel network with salinity cell 49, functions to compensate for incorrect variations in the characteristics of the cell temperature-responsive resistor (thermistor) 52 and thereby provides the degree of accuracy required in the meter readings and for the warning alarm requirements in the instant system. The value of resistor 53 may be determined by test or it may be calculated by reference to the temperature resistance curve of the temperature-responsive resistor (thermistor) 52 which is shown in detail in FIG. 2.

It is well understood in the art that the resistance of a fluid, such as water, will vary with the magnitude of concentration of dissolved and undissolved chlorides. However, the resistance characteristics of the solution will also be affected by the temperature thereof, the resistance decreasing with the increase of temperature. Since such a system as is herein involved must be unaffected by variations in the fluid temperature encountered, it is essential that the sensing element, in this case that salinity cell, be electrically compensated for variations due to temperature change in order that the output thereof be a true indication of the salinity or chloride concentration. In order to accomplish this, a thermistor 52 having a negative temperature co-efficient has been interposed in series circuit with the electrodes 55 of the conductivity cell and the physical arrangement is such that said thermistor 52 is in physical proximity to said electrodes and is simultaneously subjected to the temperature of solution under test. The thermistor 52 and electrodes 55 may be physically contained in a single cell or probe unit. However, it has been found that the temperature response characteristics of a thermistor element do not correspond to the change in resistivity caused in the fluid under test due to temperature changes. The simple thermistor curve does not approximate that of the solution under the operating temperature encountered and consequently cannot compensate thereof in and of itself.

The network, comprising the series/parallel arrangement of resistor 53 with the thermistor 52 shunted by resistor 54, provides a means of compensation in order to achieve precise meter readings and alarming. Thus, as may be seen from FIG. 2, the curve Rt represents the variations of the resistance of only the thermistor element with temperature changes. The curve Rr represents a temperature resistance curve which would provide the required correction for changes in resistivity of the fluid under test due to temperature in order to produce readings of the desired accuracy. With the incorporation of resistor 53 in series with thermistor 52, it has been found that the curve Rt is shifted to the right without any substantial change in the inclination thereof, as indicated by the curve Ra. On the other hand, if the thermistor 52 is shunted by a resistor 54 the curve is shifted to the left with some change in the inclination, as indicated by the curve Rb. The curve Rr is not characteristic of any particular solution for which correction is to be made, but represents the relative compensating changes of resistance due to temperature changes, required to produce the desired meter and alarm accuracy in the instant system.

The fluid admittance at cell electrodes 55 is detected and converted into a salinity ac signal. The salinity cell 49 functions as a voltage divider with a series-connected thermistor network 52. When the admittance of the fluid in the gap is zero, the full ac regulated bus voltage appears across the electrodes. When the fluid between the electrodes is conductive, the resulting current flow causes a voltage drop across thermistor 52. Thus, the voltage drop across the electrodes varies as a temperature-compensated function of salinity. The gap signal voltage is applied to sensor module 33, to isolation input detector 56, to meter signal bus 57 and to meter selector switch 48 on door module 17, FIG. 1E.

The isolation input detector circuit 56, FIG. 1, conditions and provides isolation of the input ac salinity signal for the alarm circuits. The negative portion of the signal is clipped and applied to a unity-gain amplifier circuit 60 with resistor 61. The input salinity signal is conditioned by input isolation resistor 58 and clipping diode 59. The signal across clipping diode 59 is applied to amplifier 60. The amplifier produces a dc signal that is proportional to the fluid salinity. The clipped output signal is then applied to a holding network consisting of diode 62, resistor 63 and capacitor 64, with sufficient time constant to develop a positive dc error signal proportional to the salinity signal. The output of the isolation input detector circuit 56 is applied to an external metering facility through resistor 128, FIG. 1A, to dump detector circuit 79, FIG. 1A, via resistor 80 and lead 82 and to alarm detector circuit 73, FIG. 1A, via resistor 65.

Within sensor module 33, a stable reference voltage supply 66, FIG. 1, is developed from the dc bus 34 using resistor 67, zener diode 68, and temperature compensation diode 69. The reference voltage supply; 66 is applied to ALARM potentiometer 70 and DUMP potentiometer 71, FIG. 1A. These controls are contained within the equipment to prevent tampering or accidental change of settings. The ALARM and DUMP potentiometers are connected in a series/parallel configuration with scaling resistor 72 to provide the following:

The signal from ALARM potentiometer 70 is an alarm reference voltage used to determine the level at which an alarm should be sent. This signal is applied to alarm detector circuit 73.

The signal from DUMP potentiometer 71 is a reference voltage used to determine the level at which the dump valves should be operated. The signal is applied to dump detector circuit 79, via resistor 83. The provision of separate DUMP and ALARM setpoints permit pre-dump alarm notification such that operating personnel can be alerted to deteriorating water conditions prior to loss of water by dumping.

The alarm detector circuit 73, FIG. 1A, compares the signal from the input detector circuit 56, FIG. 1, with the adjustable alarm reference voltage from ALARM potentiometer 70, FIG. 1A. When the salinity signal is less than the alarm reference voltage, the alarm detector circuit generates a positive level alarm signal. The alarm reference voltage is applied to comparator 74 via resistors 75 and 76. The comparator output is connected via resistors 76, 77 and 78 to form a hyesteresis loop to eliminate false triggering of comparator circuit 74.

Sensor module 33 is equipped with variable DUMP potentiometer 71, FIG. 1A, which provides a dump reference voltage for dump detector circuit 79. The dump detector circuit 79, FIG. 1A, compares the salinity signal output from input detector circuit 56, FIG. 1, with the dump reference voltage controlled by DUMP potentiometer 71, FIG. 1A. When the signal is less than the dump reference voltage, the dump detector circuit 79 generates a positive voltage dump signal. This dump reference is routed from DUMP potentiometer 71 to comparator 81, FIG. 1A, via resistor 83. The output of comparator 81 is connected to a hyesteresis network, consisting of resistors 84, 85, and 86, to prevent false triggering of the dump detector circuit 79.

When the salinity cell 49 indicates an abnormal condition (e.g. high voltage), the output of the alarm detector circuit 73 generates a positive transition level signal that is applied to alarm driver circuit 87 via lead 88, and to terminal A of switch 89, FIG. 1A. If the system is configured with switch 89 positioned between terminals A and B, the alarm signal will be applied to dump driver circuit 90, making the dump and alarm levels the same.

The alarm driver circuit 87 is a transistorized bus driver amplifier for alarm bus 94. When an alarm condition occurs, alarm driver transistor 93, with diode 95 and resistor 92, is allowed to conduct, thereby providing a return current path on alarm bus 94. The alarm bus 94 is connected to solid state relay module 35, FIG. 1B, to control the alarm signaling functions of the system.

The dump driver circuit 90, FIG. 1A, is a transistorized bus driver amplifier consisting of transistor 97 and resistor 96. When a dump condition occurs, transistor 97 is allowed to conduct, thereby providing a return current path on the dump bus 98. Under this condition, dump relay 11, FIG. 1D, will be operated, and its contacts will operate dump valve 12, FIG. 1E.

When an alarm condition occurs (and before being acknowledged), a signal output is provided to cause an indicator lamp to blink on indicator module 19, FIG. 1B. An interrupted voltage source, obtained from the blink bus 240 is applied to transistor 107 via resistor 108, FIG. 1. The output of transistor 107 is combined with the output of alarm detector 73, FIG. 1A, via resistor 120 to turn on blink gate transistor 109, FIG. 1A. This causes transistor 109, with associated diode 110 and resistor 111 to alternately conduct and turn off at the repetition rate of the blink bus. When transistor 109 is conducting, a return circuit path is provided for the corresponding red ALARM indicator lamp 121 on indicator module 19, FIG. 1B. The red ALARM indicator lamp 121 provides a visual indication of the alarm condition for the system operator. In multiple channel installations, separate indicators are provided for each salinity cell location.

An alarm gate circuit 91, FIG. 1A, is provided to maintain the blinking light display when the alarm condition is present. When an operator acknowledges the alarm, the latch is reset, and the blinking ALARM light 121 is brought to steady on. The latch circuit consists of comparator 99, FIG. 1, with its associated resistors 100, 101, 105, 113, 114, 116 and 119; diodes 102, 113A and 118; and capacitors 103, 104, 115 and 117. When an alarm condition occurs, a signal is received from alarm detector circuit 73, FIG. 1A, and sets comparator 99, FIG. 1, to provide a low at its output. When an acknowledge signal is received on the acknowledge bus 112, comparator 99 is reset to produce a positive voltage signal. The output of comparator 99 is applied to gate transistor 106 via resistor 105A. When the comparator is in the normal or acknowledge state, the blink signal appearing at the input of transistor 107 is bypassed to ground, thereby turning off transistor 107. Thus the red ALARM indicator lamp 121 on indicator module 19, FIG. 1B, will be illuminated steadily. When the salinity condition is corrected, the circuits will be reset and the ALARM indicator lamp 121 will be extinguished.

The ALARM indicator lamp 121 on the indicator module 19, FIG. 1B, may be momentarily tested by the system operator by depressing AUDIBLE CUTOUT switch 32 on door module 17, FIG. 1E. This operation provides a current return path for the ALARM indicator lamp 121, causing the lamp to illuminate. This feature also permits testing all ALARM indicator lamps to ensure that they are functional.

The alarm signal from the alarm detector circuit 73, FIG. 1A, is routed to a pulse network circuit 122 from dump detector 79, via diode 122A. The pulse circuit network consists of diode 126, capacitors 123 and 124, and resistor 125. The output of this circuit is a pulsed signal that is applied to the update bus 127.

The solid state relay module 35, FIG. 1B, decodes the alarm bus 94, the acknowledge bus 112, and the update bus 127 signals to control alarm driver 129, FIG. 1B, and bell driver 130, FIG. 1C. These drivers control the operation of alarm relay 30 and bell relay 10, FIG. 1D, respectively, to provide remote summary fault signals and an audible alarm after alarm or fault conditions have occurred. When the AUDIBLE CUTOUT switch 32 on door module 17, FIG. 1E is depressed, an acknowledge signal is applied to the acknowledge bus 112. This, in turn, de-energizes the bell 10A, FIG. 1D, thereby turning off the bell, and stops alarm lamp 121 from blinking. Operating power for the components of solid state relay module 35, FIG. 1B, is obtained from dc bus 34.

When an alarm condition occurs, the voltage signal at the input of transistor 138, FIG. 1B, from the dc bus via resistors 139 and 140 drops to zero volts. This turns off transistor 138 and opens the current return path for alarm relay 30, FIG. 1D, through resistor 143, transistor 138, FIG. 1B, and diode 141. Alarm relay 30, FIG. 1D, will then de-energize, and enable the external alarm signal. When there is no alarm condition, transistor 138, FIG. 1B, will conduct and provide a return current path for alarm relay 30, FIG. 1D.

Operational amplifiers 133 and 136, FIG. 1B, are configured with resistors 132, 134, 135, 137, 156 and 159, and capacitors 157 and 158 to form a monostable multivibrator. When an input pulse signal is received by the multivibrator, a momentary pulse is generated at the output of operational amplifier 133. This pulse is applied to transistor 142, with its associated resistors 160 and 161, diode 162, and capacitor 144, which causes transistor 142 to turn-off, thereby momentarily opening the current return path for alarm relay 30, FIG. 1D. The alarm relay 30 will open and momentarily open the external remote alarm circuit (not shown), signaling a new alarm. This provides a novel feature whereby automatic up-dating occurs so as to give faster understanding to an operator wherein subsequent alarms on salinity are sounded at the master shipbroad console and cause the local alarm bell to sound. This is in contrast to a cut-out switch which prevents or masks subsequent salinity faults.

A latch circuit, consisting of operational amplifier 145, FIG. 1B, and its associated components, including resistors 131, 146, 147, 149 and 151; capacitors 163, 164, 165 and 166; and diodes 148 and 150; is provided to generate a signal for controlling bell relay 10, FIG 1D. When an update pulse is developed at the output of operational amplifier 133, FIG. 1B, a latch set signal is applied to the input of operational amplifier 145. The output signal of operational amplifier 145 is applied to transistor 153 with its associated resistors 152 and 154 and capacitor 155, FIG. 1C. Current flow through transistor 153 will cease, thereby opening the return current path for bell relay 10, FIG. 1D, thus completing the circuit for operating the bell 10A. When an acknowledge signal is received on the acknowledge bus 112, operational amplifier 145, FIG. 1B, will be reset. The output of operational amplifier 145 will cause transistor 153, FIG. 1C, to conduct. When transistor 153 is conducting, the return current path is provided for bell relay 10, FIG. 1D, the relay will be energized, and the alarm bell 10A will be turned off.

When the sensor module 33, FIGS. 1 and 1A, applies an output alarm signal or a dump signal onto the dump bus 98, dump relay 11, FIG. 1D, is energized via diode 255, resistor 256 and capacitor 257, and power is applied to dump valve 12, FIG. 1E. When energized, dump valve 12 will shut off the flow of the contaminated fluids in the system. When dump valve 12 is in the dump state, a dump signal, via the selector arm 38 of the dump valve makes contact with the deenergized contact of dump valve 12 and connects the external power to valve position indicator module 37, FIG. 1C, for processing.

During normal operation, external ac power is applied via leads 175 and 176, FIGS. 1C and 1D, to a network consisting of resistors 177, 178, 179, 180 and 182, and diode 181, thence to photo detector 171, FIG. 1C. When a signal is applied at the input of the photo detector 171, the resistance of its internal resistor 171A will decrease. Photo detector resistor 171A is connected in a series circuit with resistors 170 and 184. The output signal of the photo detector is developed across resistor 184, and is thence applied to the input of transistor 174. Under an alarm condition, when the dump valve is de-energized, resistor 171A appears as a high resistance; the input signal to transistor 174 is reduced; and current flow is cut off through transistor 174. Transistor 168 is connected to transistor 174, via resistor 185, and will conduct at this time. Transistor 168, in turn, turns off the current flow through transistor 169, normally biased to conduct via resistor 167. The output from transistor 169 is also connected to transistor 187 via resistor 186. The output of transistor 187 is connected to dump indication line 188, FIG. 1B. When transistor 169 is not conducting, the modulated signal from the blink bus 240 is applied to valve position indicator module 37 and thence to transistor 187 via resistor 189. Thus, transistor 187 will cycle on and off at the blink bus 240 modulated cycle rate. Transistor 187 provides a circuit return for the green DUMP warning light 190 on indicator module 19, FIG. 1B, and the light will blink on and off to provide a visual indication of dumping to the system operator. Also, during an abnormal condition, the output of transistor 174, FIG. 1C, will cause transistor 192, with its associated bias resistors 172, 173 and 191, to conduct, placing an alarm signal on alarm bus 94 until the alarm condition is corrected, and dump valve 12, FIG. 1E, is manually reset.

The output of transistor 174, FIG. 1C, is also connected to a pulse network consisting of capacitors 193A and 193B, resistor 193, and diode 194. The pulse signal developed across resistor 193 is applied to the update bus 127 via diode 194. Hence, solenoid valve dumping will be signaled via the alarm relay 30.

A meter 219 on door module 17, FIG. 1G, permits a visual display of the salinity of the fluid being monitored. In multiple cell installations, a means of selecting the specific cell to be displayed is provided by means of METER SELECTOR switch 48 on the door module 17, FIG. 1E. The METER selector switch 48 consists of a single-deck rotary switch unit which provides a contact rotated by means of a knob, to select a desired salinity cell 49, FIG. 1, for display on meter 219, FIG. 1G. This selector switch can accommodate up to 10 salinity cells, in addition to an OFF position. Positioning METER SELECTOR switch 48, to a selected position will connect the monitoring curcuit of the desired cell 49. Setting the switch for the most critical location allows the operator to view trends at a distance without operating the panel. However, if desired, each salinity cell 49 may be provided with its own remote monitoring meter.

Power is supplied to solid state relay meter module 31, FIG. 1F, from the dc bus 34, and routed through parallel current limiting resistors 195 and 196 to provide a +30 vdc power source. Dc bus power is also connected to a regulator network consisting of resistor 199, zener diode 201 and filter capacitor 200 to provide a +14 vdc supply for some of the module components. A −14 vdc supply for the module components is derived from the −30 vdc bus 42, FIG. 1E, using a regulator circuit consisting of resistor 202, FIG. 1F, capacitor 203 and zener diode 204.

A constant current generator 198, FIG. 1F, is provided to generate a calibrated current source to test the accuracy of meter 219, FIG. 1G, by causing a predetermined scale reading on the meter when METER TEST switch 216, FIG. 1G, is depressed. The constant current generator 198, FIG. 1F, consists of resistors 210 and 213, zener diode 209, transistor 214 and diodes 211 and 212, with calibrating potentiometer 215. When METER TEST switch 216, FIG. 1G, is depressed, the output of the constant current generator 198 is applied to the momentary contact 217 of switch pole 218, thence to meter (plus) terminal 220. The return circuit for the meter is signal common 39.

A salinity signal from the salinity cell is applied to solid state relay meter module 31, FIG. 1F, via the contacts of METER SELECTOR switch 48, FIG. 1E. The salinity signal is first amplified by operational amplifier 223, with resistors 221 and 224 and capacitor 222, then applied to difference amplifier 205, consisting of operational amplifier 206 with resistors 225, 226, 227 and 228. Thus, an ac voltage, proportional to the cell salinity is developed across the temperature compensator network. This signal is applied to operational amplifier 229. Operational amplifier 229 provides for removing the negative-going portion of the previously amplified signal, via diode 230. The output signal of operational amplifier 229 is filtered to remove any ripple component, by means of filter capacitor 233 and resistors 231 and 232, FIG. 1G. The filtered signal is then applied to follower operational amplifier 208 and resistor 234. The output of operational amplifier 208 is applied to meter 219 via series resistor 235, meter calibration adjustment potentiometer 236, and METER TEST switch 216. Meter calibration adjustment potentiometer 236, permits a means of adjusting the meter indication to compensate for variations between individual components.

A blink circuit 197, FIG. 1F, is comprised of various interconnected components, including resistors 241, 242, 249, 253 and 254 and capacitors 245, 246, 247, 250, 251 and 252, and transistors 244 and 248 to form a free-running multivibrator circuit that develops a pulse train. The pulse rate is at a rate that, when applied to a door panel indicator, will give the operator a perceptable on and off flashing of the indicator. The output of the multivibrator is applied to emitter-follower amplifier transistor 243, thence to blink bus 240 for system use.

On door module 17, FIG. 1E, SIMULATED INPUT CONTROL potentiometer 47 provides the capability to generate a simulated signal that is used for duplicating the signal from salinity cell 49, FIG. 1. An ac regulated voltage is connected across SIMULATED INPUT CONTROL potentiometer, 47, FIG. 1E, and an output voltage is tapped by wiper arm 237, and subsequently connected to SIMULATED INPUT TEST switch 238. When SIMULATED INPUT TEST switch 238 is depressed, a signal is applied to current limiting resistor 239, FIG. 1E, and to solid state relay module 31, FIG. 1F. The simulated signal will be processed by solid state relay module 31 in the same manner as a salinity cell signal. Thus, a means of setting or checking the alarm level of the salinity cell as well as ALARM potentiometer 70, and DUMP potentiometer 71, FIG. 1A, without disturbing the input connections.

While I have described and illustrated one specific embodiment of my invention, it will be clear that variations of the details of construction which are specifically illustrated and described may be resorted to without departing from the true spirit and scope of the invention as defined in the appended claims.

What is claimed is:

1. A salinity indicator system for monitoring and indicating the salinity of a water source comprising:
   a salinity cell adapted to sense changes in the salinity of the said water,
   a regulated A.C. source of voltage for application to said salinity cell, an input detector circuit connected to receive the salinity signal generated by said salinity cell, an alarm detector circuit connected to receive the output from said input detector circuit, a dump detector circuit connected to receive the output from said input detector circuit, an alarm driver circuit connected to receive the output from said alarm detector circuit, an alarm relay connected to receive the output from said alarm driver circuit, a bell driver circuit connected to receive the output from said alarm relay, a bell relay connected to receive the output from said bell driver circuit, an alarm bell connected to receive the output from said bell relay, switch means capable of being selectively connected to the output of said alarm detector circuit or said dump detector circuit, a dump driver circuit selectively connected through said switch means to the output of either said alarm detector circuit or said dump detector circuit, a dump relay connected to receive the output from said dump driver circuit, a dump valve connected to receive the output from said dump relay, an indicator circuit connected to said alarm relay circuit for indicating an alarm condition, and a meter connected to receive the output from said salinity cell to provide a reading of the salinity of said water.

2. The salinity indicator system according to claim 1 wherein said salinity cell comprises a conductivity cell, and a temperature compensating thermistor and resistor network connected in circuit with said conductivity cell wherein said resistors are located and mounted inside said conductivity cell.

3. The salinity indicator system according to claim 2 wherein said temperature compensating thermistor and resistor network comprises a series-parallel arrangement including a resistor connected in parallel with a series arangement of a registor and a thermistor.

4. The salinity indicator system according to claim 1 wherein said alarm detector circuit comprises an alarm potentiometer connected to receive the output from said input detector circuit, and said dump detector circuit comprises a dump potentiometer connected to receive the output from said input detector circuit.

5. The salinity indicator system according to claim 4 wherein said alarm potentiometer and said dump potentiometer are connected in parallel configuration with each other to receive the output from said input detector circuit.

6. The salinity indicator system according to claim 5 wherein said alarm potentiometer is set at a level different from said dump potentiometer whereby said alarm will activate prior to actual loss of water by dumping action.

7. The salinity indicator system according to claim 6 further comprising a hysteresis network connected to said dump detector circuit to prevent false triggering of said dump detector circuit.

8. The salinity indicator system according to claim 4 further comprising a hysteresis circuit connected to said alarm detector circuit to prevent false triggering of said alarm detector circuit.

9. The salinity indicator system according to claim 1 further comprising an indicator lamp connected in circuit with said alarm detector circuit, and a pulse network connected in circuit with said alarm detector circuit and said indicator lamp, whereby an alarm condition causes said indicator lamp to blink thereby providing a visual indication of the alarm condition.

10. The salinity indicator system according to claim 9 further comprising an alarm gate circuit connected to said indicator lamp and to said alarm detector circuit, and acknowledge switch means connected to said alarm gate circuit for transmitting an alarm acknowledge signal to said alarm gate circuit and said indicator, whereby the blinking indicator light caused by said alarm condition converts to a steady on light until said salinity condition is corrected.

11. The salinity indicator system according to claim 10 further comprising a connection between said acknowledge switch and said bell alarm, whereby throwing said switch de-energizes said alarm bell simultaneously with the conversion of the blinking alarm indicator lamp to a steady on condition.

12. The salinity indicator system according to claim 1 further comprising a monostable multivibrator circuit connected to receive an output from said alarm driver circuit, an alarm relay driver circuit connected to receive an output from said monostable multivibrator, said alarm relay driver being connected to said alarm relay whereby an input pulse signal received by said monostable multivibrator pulses said alarm relay driver causing said alarm relay to momentarily open thereby signaling another alarm condition in said system.

13. The salinity indicator system according to claim 9 further comprising a dump warning circuit connected to said pulse network, a dump warning light connected to said dump warning circuit whereby actuation of said dump valve upon the occurrence of an alarm condition causes said dump warning light to blink to provide a visual indication of dumping by the system.

14. The salinity indicator system according to claim 1 wherein said salinity cell comprises a plurality of salinity cells for monitoring the salinity of a plurality of separate water sources, and further comprising a multi-position selector switch connected between said salinity cell and said meter whereby said meter may be selectively connected to any of the plurality of salinity cells.

15. The salinity indicator system according to claim 1 further comprising a meter test generator circuit for generating a test signal to be applied to said meter and a meter test switch connected to said meter test signal generator circuit and said meter for selectively connecting one to the other, whereby actuation of said meter test switch generates and applies to said meter a test signal whereby the accuracy of said meter may be tested.

16. The salinity indicator system according to claim 1 further comprising a meter calibration adjustment potentiometer for adjusting said meter to compensate for variations in the system components.

* * * * *